US011606607B2

(12) United States Patent
Huang et al.

(10) Patent No.: US 11,606,607 B2
(45) Date of Patent: Mar. 14, 2023

(54) HOME INFOTAINMENT SYSTEM HAVING FUNCTION OF NON-CONTACT IMAGING-BASED PHYSIOLOGICAL SIGNAL MEASUREMENT

(71) Applicant: FaceHeart Inc., Hsinchu (TW)

(72) Inventors: Chung-Shine Huang, Zhubei (TW); Tsuey-Huey Shiue, Hsinchu (TW)

(73) Assignee: FACEHEART INC., Hsinchu (TW)

( * ) Notice: Subject to any disclaimer, the term of this patent is extended or adjusted under 35 U.S.C. 154(b) by 345 days.

(21) Appl. No.: 17/004,336

(22) Filed: Aug. 27, 2020

(65) Prior Publication Data

US 2021/0227289 A1    Jul. 22, 2021

(30) Foreign Application Priority Data

Jan. 21, 2020   (TW) ................................ 109102291

(51) Int. Cl.
| | |
|---|---|
| *H04N 21/442* | (2011.01) |
| *A61B 5/00* | (2006.01) |
| *A61B 5/0205* | (2006.01) |
| *A61B 5/02* | (2006.01) |
| *A61B 5/029* | (2006.01) |

(Continued)

(52) U.S. Cl.
CPC ..... *H04N 21/44218* (2013.01); *A61B 5/0002* (2013.01); *A61B 5/0205* (2013.01); *A61B 5/02007* (2013.01); *A61B 5/029* (2013.01); *A61B 5/1118* (2013.01); *A61B 5/1176* (2013.01); *A61B 5/14551* (2013.01); *A61B 5/4368* (2013.01); *A61B 5/4393* (2013.01); *A61B 5/6887* (2013.01); *A61B 5/743* (2013.01); *G06V 40/168* (2022.01); *G06V 40/172* (2022.01); *H04N 21/4223* (2013.01); *H04N 21/42201* (2013.01); *A61B 5/021* (2013.01); *A61B 5/02405* (2013.01); *A61B 5/0816* (2013.01)

(58) Field of Classification Search
None
See application file for complete search history.

(56) References Cited

U.S. PATENT DOCUMENTS

| | | | |
|---|---|---|---|
| 2013/0079097 A1* | 3/2013 | Nicely | G07F 17/323 463/16 |
| 2016/0086500 A1* | 3/2016 | Kaleal, III | G06T 19/00 434/257 |

(Continued)

*Primary Examiner* — Eileen M Adams (57) ABSTRACT

The present invention discloses a home infotainment system having function of non-contact imaging-based physiological signal measurement. In the present invention, an image-based physiological signal (IBPS) measuring device is integrated with a television, and is configured for capture at least one image frame of a user who is watching the television. As such, after detecting detects a face portion from the image frame, the IBPS measuring device is able to subsequently extract at least one physiological signal from the face portion. Consequently, after the physiological signal is applied with at least one signal process by a display processor of the television or the IBPS measuring device, physiological indices of the user are hence calculated, and are subsequently applied with data processes of data storing, data transmitting, and/or displaying the physiological indices by a form of graphs, or diagrams, and/or numeric values.

13 Claims, 10 Drawing Sheets

(51) Int. Cl.
*A61B 5/1455* (2006.01)
*A61B 5/11* (2006.01)
*A61B 5/1171* (2016.01)
*H04N 21/4223* (2011.01)
*H04N 21/422* (2011.01)
*G06V 40/16* (2022.01)
*A61B 5/08* (2006.01)
*A61B 5/024* (2006.01)
*A61B 5/021* (2006.01)

(56) References Cited

U.S. PATENT DOCUMENTS

2017/0163946 A1* 6/2017 Komanduri ............. F21V 13/08
2018/0192900 A1* 7/2018 Wei ........................ G06F 21/31

* cited by examiner

HOME INFOTAINMENT SYSTEM HAVING FUNCTION OF NON-CONTACT IMAGING-BASED PHYSIOLOGICAL SIGNAL MEASUREMENT

BACKGROUND OF THE INVENTION

1. Field of the Invention

The present invention relates to the technology field of home healthcare service, and more particularly to a home infotainment system having function of non-contact imaging-based physiological signal measurement.

2. Description of the Prior Art

Blood oxygen concentration and heart rate are known two of important indices for judging human health state. Nowadays, photoplethysmography (PPG) is a simple and low-cost optical technique that is found being capable of carrying out a physiological measurement for an individual. For example, Taiwan patent No. 1592138 has disclosed a wearable blood-pressure measuring device. The disclosed wearable blood-pressure measuring device is a currently best-selling smart wristband, and is configured for utilizing the PPG method to complete a physiological measurement for a user who wears the smart wristband on his wrist. On the other hand, U.S. patent publication No. 2017/0340217 A1 has disclosed a physiological detection device. The disclosed physiological detection device is a fingertip pulse oximeter, and has an accommodation space for receiving a user's forefinger, such that the physiological detection device emits a detecting light toward one surface of the forefinger, and then receives a transmitted light from another one surface of the forefinger. Consequently, the physiological detection device obtains a photoplethysmographic (PPG) signal after successively receiving the transmitted light.

From above descriptions, it is understood that the PPG method has been widely applied in contact light-reflection type physiological measuring devices and/or contact light-transmission type physiological measuring devices. However, experience of really operating the conventional contact type physiological measuring devices indicates that, the conventional contact type physiological measuring devices exhibits many disadvantages in practical use. First, allergic contact dermatitis occurs on the user's wrist when the wrist skin comes into direct contact with the contact type physiological measuring device for a specific time. On the other hand, the user certainly fails to execute daily physiological measurement and personal health management in case of forgetting to wear his smartwatch or smart wristband.

It is worth mentioning that, various smart home appliances are constantly innovated with the advanced progress of IoT (Internet of Things) technologies. Smart TV is one kind of smart home appliance, and is also a basic home infotainment device. It is a pity that, however, the commercial smart TVs merely have functionalities of displaying movies and television programs, Internet linking, and playing video games, the commercial smart TVs still lack the import functionalities of executing daily physiological measurement and managing home members' personal health information.

From above descriptions, it is clear that the conventionally-commercial smart TVs still have plenty of room for improvement of the home healthcare services. In view of that, inventors of the present application have made great efforts to make inventive research and eventually provided a home infotainment system having function of non-contact imaging-based physiological signal measurement.

SUMMARY OF THE INVENTION

The primary objective of the present invention is to disclose a home infotainment system having function of non-contact imaging-based physiological signal measurement, comprising: a display unit such as a television and an image-based physiological signal (IBPS) measuring device. Particularly, the IBPS measuring device comprises an image capturing module and a core processor module, wherein the core processor module is provided with a sensing portion detecting unit and a physiological index calculating unit therein. In the present invention, the image capturing module is configured for facing at least one user who is watching the television, so as to capture at least one image frame of the user. As such, after the sensing portion detecting detects a face portion from the image frame, the physiological index calculating unit subsequently extracts at least one physiological signal from the face portion. Therefore, after the physiological signal is applied with at least one signal process by a display processor of the television or the physiological index calculating unit of the IBPS measuring device, physiological indices of the user are hence calculated, and are subsequently applied with data processes of data storing, data transmitting, and/or displaying the physiological indices by a form of graphs, or diagrams, and/or numeric values.

In order to achieve the forgoing primary objective, the present invention provides a first embodiment for the home infotainment system having function of non-contact imaging-based physiological signal measurement, comprising:

a television; and an image-based physiological signal (IBPS) measuring device, being coupled to a display processor of the television, and comprising an image capturing module that is configured for facing at least one user who is watching the television, so as to capture at least one image frame of the user; wherein the IBPS device further comprises a core processor module coupled to the image capturing module, and the core processor module comprising:

a sensing portion detecting unit, being used for receiving the at least one image frame that is transmitted from the image capturing module, thereby detecting a face portion from the image frame; and a physiological index calculating unit, being coupled to the sensing portion detecting unit, and being configured for extracting at least one physiological signal from the face portion, so as to subsequently calculate a plurality of physiological indices after applying at least one signal process to the physiological signal.

Moreover, the present invention also provides a second embodiment for the home infotainment system having function of non-contact imaging-based physiological signal measurement, comprising:

a display device;

a video stream providing device, being coupled to a display source, and being used for making the display device to display a video based on the display source; and an image-based physiological signal (IBPS) measuring device, being coupled to a display processor of the video stream providing device, and comprising an image capturing module that is configured for facing at least one user who is watching the television, so as to capture at least one image frame of the user; wherein the IBPS device further comprises a core processor module coupled to the image capturing module, and the core processor module comprising:

a sensing portion detecting unit, being used for receiving the at least one image frame that is transmitted from the image capturing module, thereby detecting a face portion from the image frame; and a physiological index calculating unit, being coupled to the sensing portion detecting unit, and being configured for extracting at least one physiological signal from the face portion, so as to subsequently calculate a plurality of physiological indices after applying at least one signal process to the physiological signal.

In the first embodiment and the second embodiment of the forgoing home infotainment system, the plurality of physiological indices comprises heart rate heart rate, respiratory rate, heart rate variability (HRV), blood volume, arterial oxygen saturation, blood pressure, blood vessel viscosity, venous function, venous reflux, ankle pressure, genital response, and cardiac output, and the core processor module further applying a data process to the plurality of physiological indices, wherein the data process is selected from the group consisting of data storing, data transmitting, displaying the physiological indices by a form of graphs or diagrams, and displaying the physiological indices by a form of numeric values.

In the first embodiment and the second embodiment of the forgoing home infotainment system, the IBPS measuring device is an independent camera device comprising the core processor module and a communication module, such that the IBPS measuring device is able to transmit the plurality of physiological indices to the display processor of the television.

In the first embodiment, the home infotainment system can be integrated in the television, such that the display processor is able to further applying a data process to the plurality of physiological indices that are transmitted from the core processor module, wherein the data process is selected from the group consisting of data storing, data transmitting, displaying the physiological indices by a form of graphs or diagrams, and displaying the physiological indices by a form of numeric values.

In the first embodiment of the forgoing home infotainment system, the television is selected from the group consisting of LCD display device, LED display device, QD-LED display device, and OLED display device.

In the second embodiment of the forgoing home infotainment system, the video stream providing device is selected from group consisting of digital set-up box, home video game console and projection device, and the display device is selected from the group consisting of television, projection screen, LCD display device, LED display device, QD-LED display device, and OLED display device.

In the first embodiment and the second embodiment of the forgoing home infotainment system, the IBPS measuring device further comprises a main controller module, and the main controller module is coupled to the image capturing module, the core processor module and the communication module for controlling an operation of the image capturing module and an operation of the core processor module and a data transmission between the communication module and the display processor.

In the first embodiment and the second embodiment of the forgoing home infotainment system, the core processor module further comprises an activity index calculating unit, and the activity index calculating unit being coupled to the physiological index calculating unit, so as to calculate a plurality of activity indices of the user based on the plurality of physiological indices.

In the first embodiment and the second embodiment of the forgoing home infotainment system, the IBPS measuring device further comprises a storage module, and the storage module being coupled to the core processor module and the main controller module, so as to store the plurality of activity indices and/or the plurality of physiological indices.

In the first embodiment and the second embodiment of the forgoing home infotainment system, the core processor module further comprises a face recognition unit, and the face recognition unit being coupled to the sensing portion detecting unit, so as to extract at least one facial feature of the user from the face portion that is found out by the sensing portion detecting unit, thereby completing a comparison between a plurality of reference facial features that are stored in the storage module and the facial feature.

In the first embodiment and the second embodiment of the forgoing home infotainment system, the storage module comprises:

a first data base for storing a plurality of user identity lists and the plurality of reference facial features, wherein each of the plurality of user identity lists has the corresponding reference facial features thereof; and a second data base for storing the plurality of activity indices and the plurality of physiological indices according to the plurality of user identity lists.

In the first embodiment and the second embodiment of the forgoing home infotainment system, the core processor module further comprises a health state evaluating unit, and the health state evaluating unit being coupled to the activity index calculating unit and the physiological index calculating unit, so as to complete a health state evaluation of the user based on the plurality of activity indices and the plurality of physiological indices.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

To more clearly describe a home infotainment system having function of non-contact imaging-based physiological signal measurement disclosed by the present invention, embodiments of the present invention will be described in detail with reference to the attached drawings hereinafter.

First Embodiment

Figure 1:
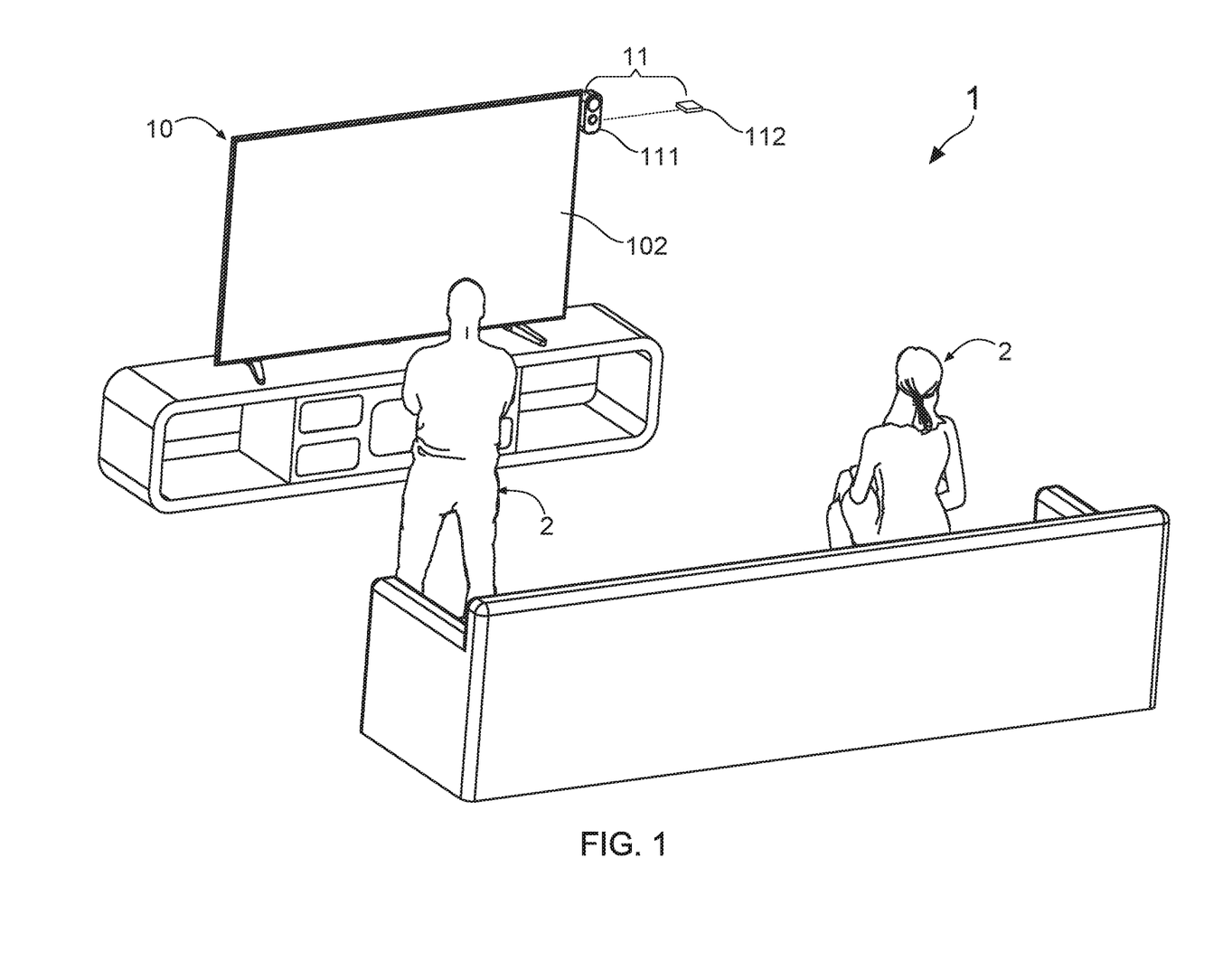
FIG. 1 shows a first stereo diagram of a home infotainment system having function of non-contact imaging-based physiological signal measurement according to the present invention.
Figure 2:
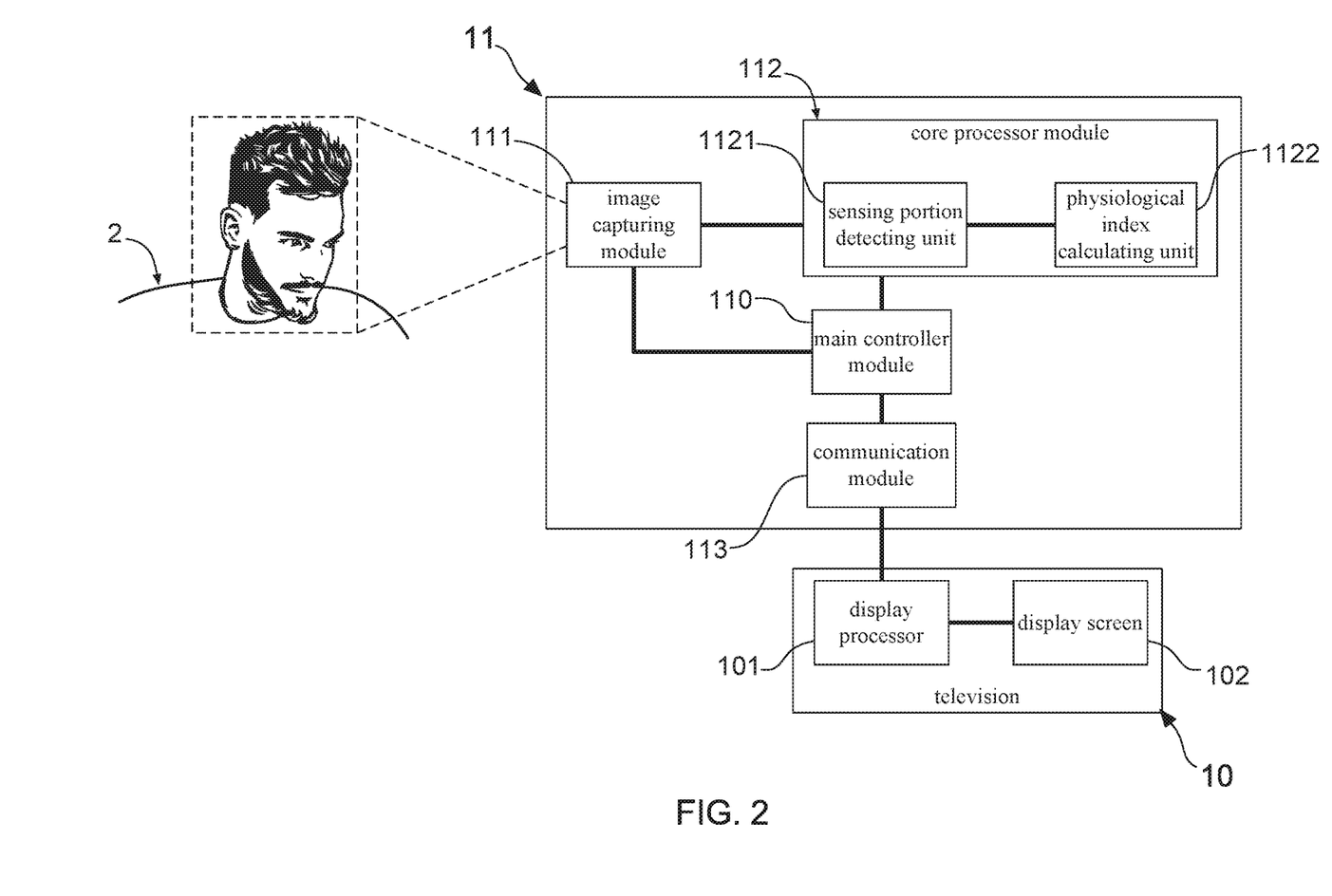
FIG. 2 shows a first block diagram of the home infotainment system having function of non-contact imaging-based physiological signal measurement according to the present invention.

With reference to FIG. 1, there is shown a first stereo diagram of a home infotainment system having function of non-contact imaging-based physiological signal measurement according to the present invention. Moreover, FIG. 2 illustrates a first block diagram of the home infotainment system having function of non-contact imaging-based physiological signal measurement. In the first embodiment, the home infotainment system 1 is configured to have a function of non-contact imaging-based physiological signal measurement, and mainly comprises: a television 10 and an image-based physiological signal (IBPS) measuring device 11, wherein the television 10 can be an LCD display device, an LED display device, a QD-LED display device, or an OLED display device. It needs to particularly explain that, the IBPS measuring device 11 in the first embodiment is an independent camera device that comprises an image capturing module 111, a core processor module 112 and a communication module 113. However, the IBPS measuring device 11 is not limited to be the independent camera device comprising one image capturing module 111, one core processor module 112 and one communication module 113. From example, in a practicable embodiment, the IBPS measuring device 11 can be integrated in the television 10.

As described in more detail below, the IBPS measuring device 11 is coupled to a display processor 101 of the television 10, and is configured for facing at least one user 2 who is watching the television 10, so as to capture at least one image frame of the user 2. In other words, the present invention particularly design the IBPS measuring device 11 to complete an image capture procedure in case of the user 2 being watching television 10. As such, after detecting detects a face portion from at least one image frame of the user 2, the IBPS measuring device 11 is able to subsequently extract at least one physiological signal from the face portion. Consequently, the IBPS measuring device 11 calculates a plurality of physiological indices after applying at least one signal process to the physiological signal. FIG. 1 and FIG. 2 also depict that the IBPS measuring device 11 comprises a main controller module 110, an image capturing module 111, a core processor module 112, and a communication module 113. The main controller module 110 is coupled to the communication module 113, such that the main controller module 110 is able to transmit the plurality of physiological indices to the display processor 101 of the television 10. In one practicable embodiment, the communication module 113 comprises a wired transmission interface and/or wireless transmission interface.

In the first embodiment, the main controller module 110 is coupled to the image capturing module 111, the core processor module 112 and the communication module 113 for controlling an operation of the image capturing module 111 and an operation of the core processor module 112 and a data transmission between the communication module 113 and the display processor 101. It is worth noting that, the core processor module 112 are provided with a sensing portion detecting unit 1121 and a physiological index calculating unit 1122. It should be understood that, because the said core processor module 112 is an electronic chip that is integrated in the IBPS measuring device 11, the sensing portion detecting unit 1121 and the physiological index calculating unit 1122 can be provided in the signal core processor module 112 by a form of firmware, function library, application program, or operands.

As described in more detail, the sensing portion detecting unit 1121 is used for receiving the at least one image frame that is transmitted from the image capturing module 111, thereby detecting a face portion from the image frame. On the other hand, the physiological index calculating unit 1122 is coupled to the sensing portion detecting unit 1121, and is configured for extracting at least one physiological signal from the face portion, so as to subsequently calculate a plurality of physiological indices after applying at least one signal process to the physiological signal. In a practicable embodiment, the physiological indices comprises: heart rate, respiratory rate, heart rate variability (HRV), blood volume, arterial oxygen saturation, blood pressure, blood vessel viscosity, venous function, venous reflux, ankle pressure, genital response, and cardiac output. Herein, it needs to further explain that, the sensing portion detecting unit 1121 is also configured for detecting a chest portion from the image frame, such that physiological index calculating unit 1122 is able to extract the physiological signal from the chest portion, so as to subsequently calculate a respiratory rate of the user 2.

Figure 3:
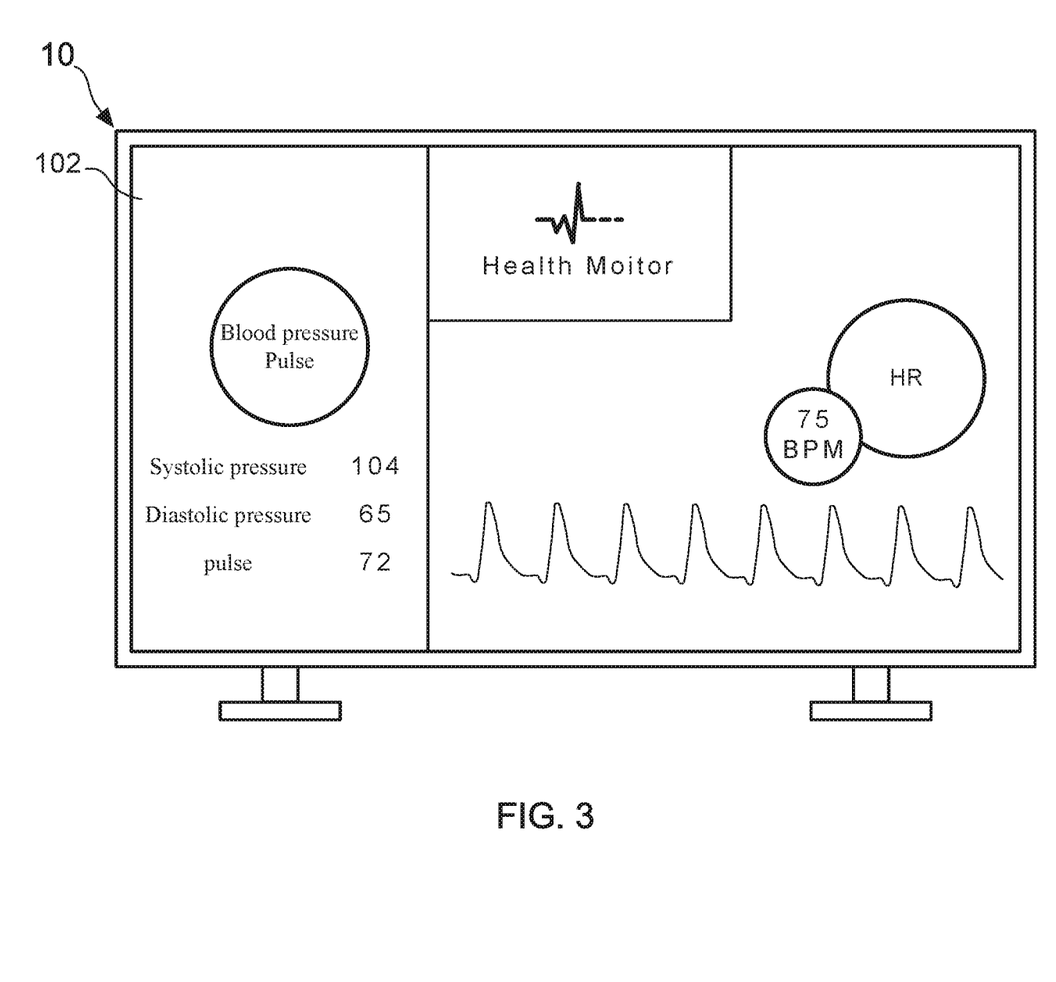
FIG. 3 shows a front view of a television.

Continuously referring to FIG. 1 and FIG. 2, and please simultaneously refer to FIG. 3 showing a front view of the television 10. After obtaining the plurality of physiological indices, the core processor module 112 further applies a data process to the physiological indices, wherein the data process is selected from the group consisting of data storing, data transmitting, displaying the physiological indices by a form of graphs or diagrams, and displaying the physiological indices by a form of numeric values. However, in a practicable embodiment, the core processor module 112 transmits the plurality of physiological indices to the display processor 101 of the television 10 without applying the data process to the physiological indices. As a result, the display processor 101 applies the forgoing data process to the physiological indices. For example, FIG. 3 depicts that a display screen 102 of the television 10 displays the physiological indices by a form of graphs, diagrams, and/or numeric values.

Moreover, besides displaying the physiological indices by a form of graphs, diagrams, and/or numeric values, the television 10 (i.e., a smart TV) can also further upload the physiological indices to a cloud server, thereby achieving a cloud management service for home healthcare.

Second Embodiment

Figure 4:
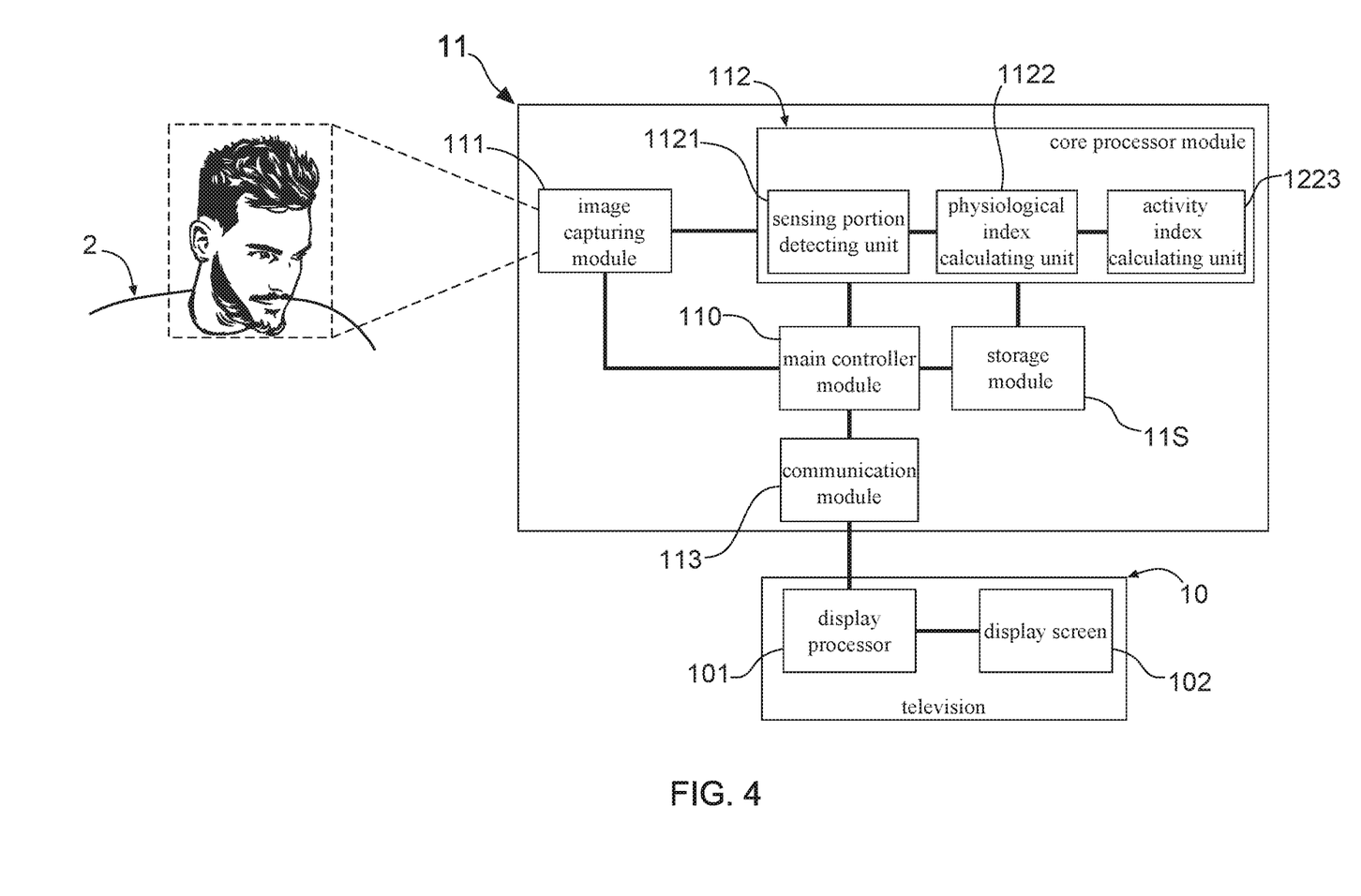
FIG. 4 shows a second block diagram of the home infotainment system having function of non-contact imaging-based physiological signal measurement according to the present invention.

FIG. 4 shows a second block diagram of the home infotainment system having function of non-contact imaging-based physiological signal measurement according to the present invention. After comparing FIG. 4 with FIG. 2, it is understood that, the home infotainment system 1 also comprises a television and an IBPS measuring device 11. In second embodiment, the IBPS measuring device 11 comprises a controller module 110, an image capturing module 111, a core processor module 112, a communication module 113, and a storage module 11S. In addition, the core processor module 112 is further provided with an activity index calculating unit 1123 therein. FIG. 4 depicts that the activity index calculating unit 1123 is coupled to the physiological index calculating unit 1122, so as to calculate a plurality of activity indices of the user 2 based on the plurality of physiological indices. Therefore, the plurality of activity indices and/or the plurality of physiological indices are stored in the storage module 11S that is coupled to the core processor module 112 and the main controller module 110. Of course, the core processor module 112 is able to transmit the plurality of physiological indices and/or the plurality of physiological indices that are stored in the storage module 11S to the television 10, thereby making the display screen 102 of the television 10 displays the physiological indices by a form of graphs, diagrams, and/or numeric values.

Third Embodiment

Figure 5:
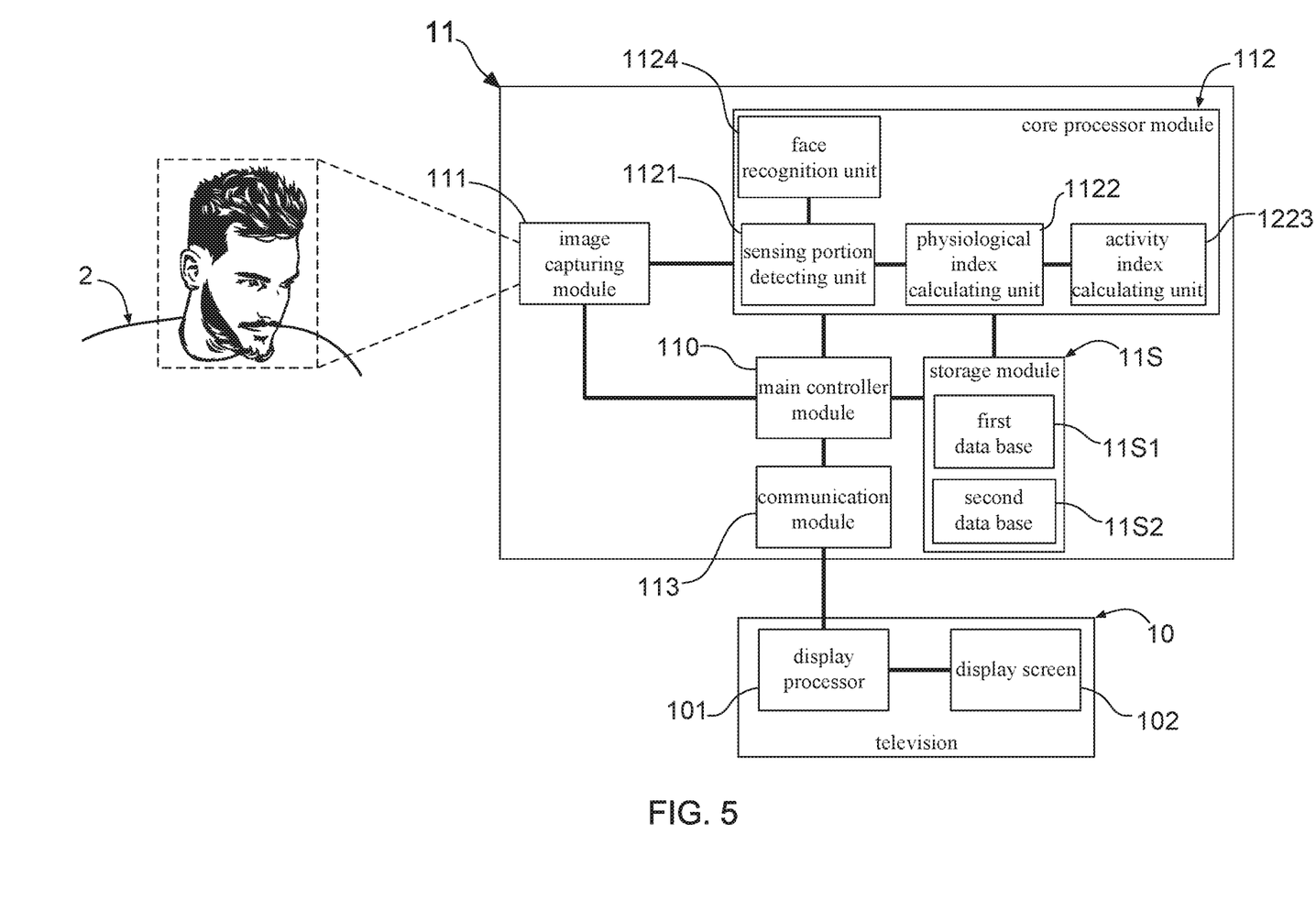
FIG. 5 shows a third block diagram of the home infotainment system having function of non-contact imaging-based physiological signal measurement according to the present invention.

FIG. 5 shows a third block diagram of the home infotainment system having function of non-contact imaging-based physiological signal measurement according to the present invention. After comparing FIG. 5 with FIG. 4, it is understood that, the home infotainment system 1 also comprises a television and an IBPS measuring device 11, and the IBPS measuring device 11 comprises a controller module 110, an image capturing module 111, a core processor module 112, a communication module 113, and a storage module 11S. In third embodiment, the core processor module 112 is further provided with a face recognition unit 1124 therein, wherein the face recognition unit 1124 is coupled to the sensing portion detecting unit 1121, so as to extract at least one facial feature of the user 2 from the face portion that is found out by the sensing portion detecting unit 1121, thereby completing a comparison between a plurality of reference facial features that are stored in the storage module 11S and the facial feature.

As described in more detail below, FIG. 5 also depicts that the storage module 11S comprises a first data base 11S1 and a second data base 11S2. In which, the first data base is adopted for storing a plurality of user identity lists and the plurality of reference facial features, wherein each of the plurality of user identity lists has the corresponding reference facial features thereof. From example, in case of the user identity lists contain grandpa, grandma, father, mother, and children, the first data base 11S would store face features corresponding to each of the home members. On the other hand, the second data base 1152 is used for storing the plurality of activity indices and the plurality of physiological indices according to the plurality of user identity lists.

Fourth Embodiment

Figure 6:
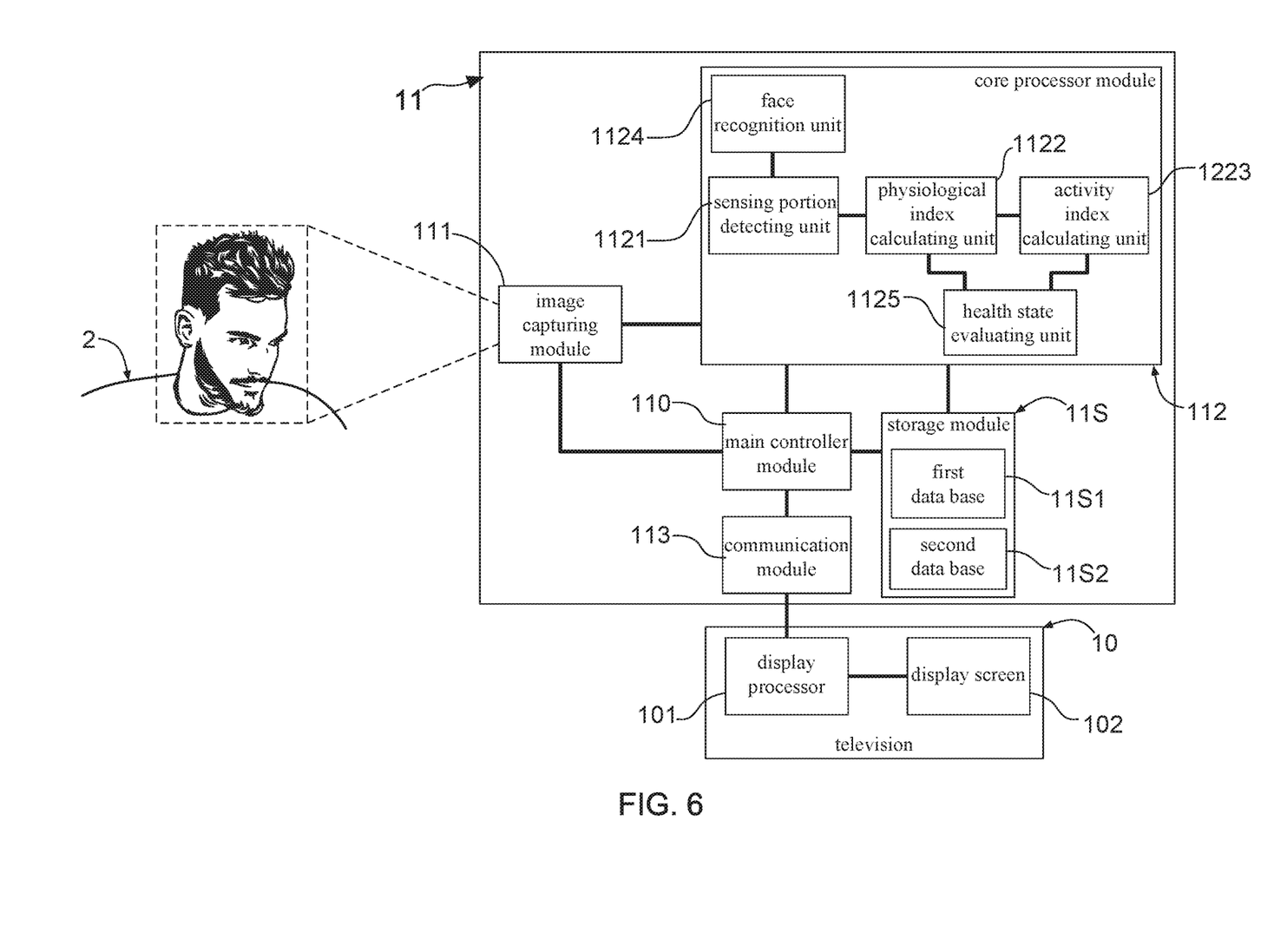
FIG. 6 shows a fourth block diagram of the home infotainment system having function of non-contact imaging-based physiological signal measurement according to the present invention.

FIG. 6 shows a fourth block diagram of the home infotainment system having function of non-contact imaging-based physiological signal measurement according to the present invention. After comparing FIG. 6 with FIG. 5, it is understood that, the home infotainment system 1 also comprises a television and an IBPS measuring device 11, and the IBPS measuring device 11 comprises a controller module 110, an image capturing module 111, a core processor module 112, a communication module 113, and a storage module 11S. In fourth embodiment, the core processor module 112 is further provided with a health state evaluating unit 1125, wherein the health state evaluating unit 1125 is coupled to the activity index calculating unit 1123 and the physiological index calculating unit 1122, so as to complete a health state evaluation of the user 2 based on the plurality of activity indices and the plurality of physiological indices. According to the particular design of the present invention, in case of the health state evaluating unit 1125 finding that any one of the user 2 not exhibits a normal heath state, the health state evaluating unit 1125 immediately transmits a warning signal to the core processor 101 of the television 10, such that the core processor 101 makes the display screen 102 show the warning signal to the user 2 by a form of text, pattern, or symbol.

Fifth Embodiment

Figure 7:
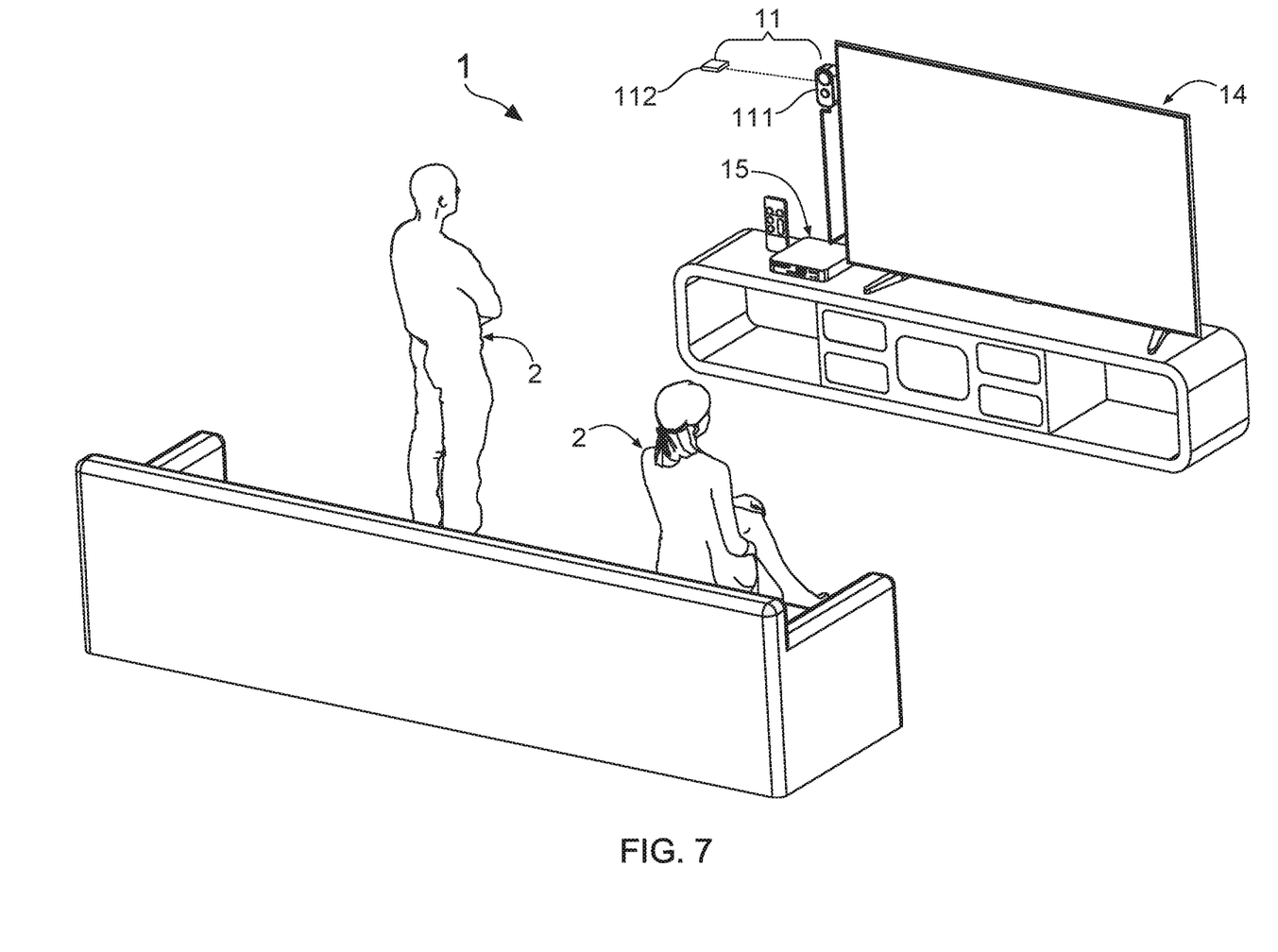
FIG. 7 shows a second stereo diagram of the home infotainment system having function of non-contact imaging-based physiological signal measurement according to the present invention.
Figure 8:
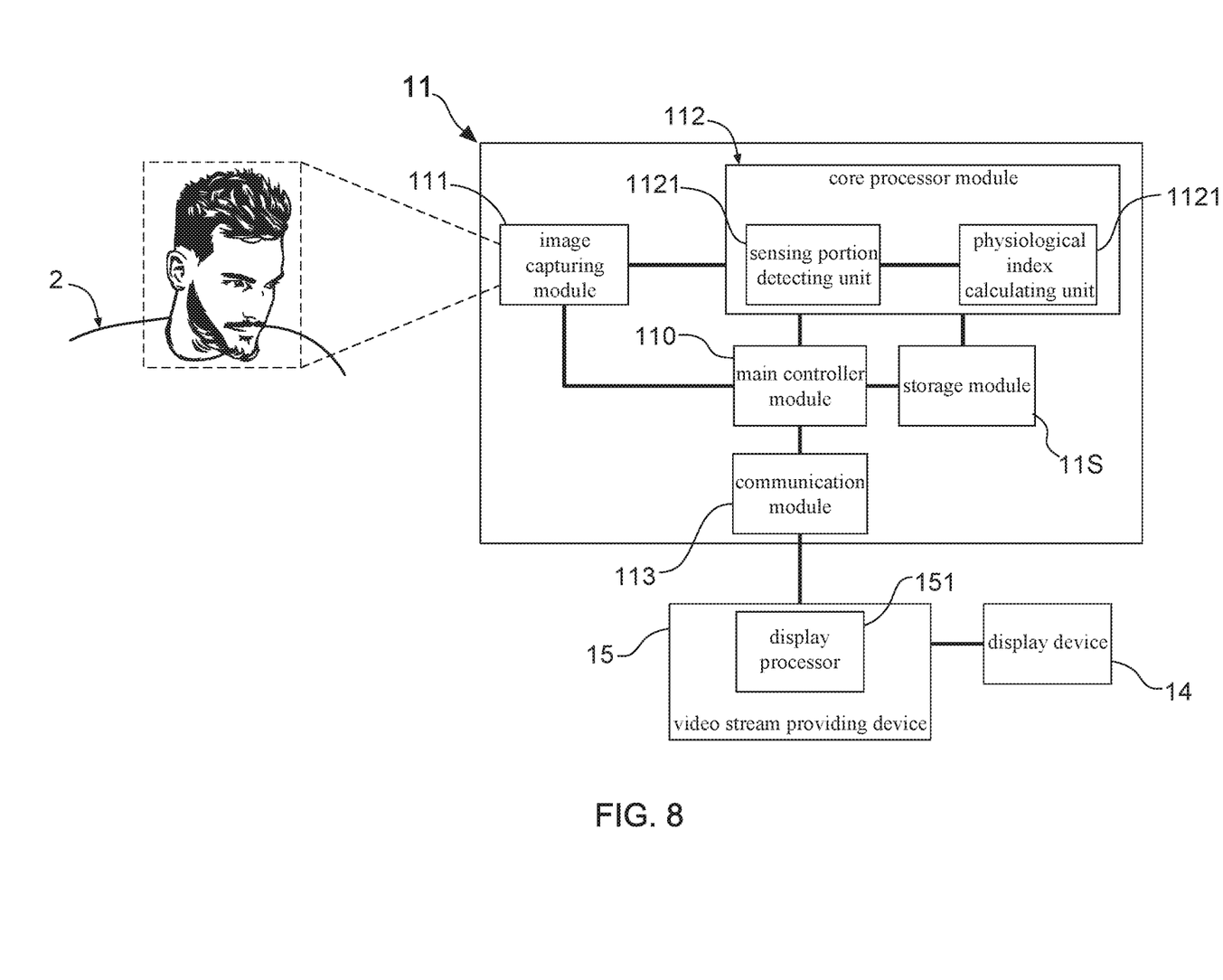
FIG. 8 shows a fifth block diagram of the home infotainment system having function of non-contact imaging-based physiological signal measurement according to the present invention.

With reference to FIG. 7, there is shown a second stereo diagram of the home infotainment system having function of non-contact imaging-based physiological signal measurement according to the present invention. Moreover, FIG. 8 illustrates a fifth block diagram of the home infotainment system having function of non-contact imaging-based physiological signal measurement. Differing from the fact that the above-described first embodiment of the home infotainment system 1 comprises a television 10 and an IBPS measuring device 11, in the fifth embodiment, the home infotainment system 1 is particularly designed to comprise a display device 14, a video stream providing device 15, and the forgoing image-based physiological signal (IBPS) measuring device 11. As described in more detail below, FIG. 7 depicts that the video stream providing device 15 is a digital set-up box (STB), and the display device 14 is a television. Therefore, it should be understood that, the video stream providing device 15 (STB) is coupled to a display source, so as to make the display device 14 to display a video based on the display source.

As FIG. 8 shows, the IBPS measuring device 11 is coupled to a display processor 151 of the video stream providing device 15, and comprising an image capturing module 111, a core processor 112, a communication module 113, and a storage module 11S. In the fifth embodiment, the physiological index calculating unit 1122 is coupled to the sensing portion detecting unit 1121, and is configured for extracting at least one physiological signal from the face portion, so as to subsequently calculate a plurality of physiological indices after applying at least one signal process to the physiological signal. As a result, the core processor module 112 transmits the plurality of physiological indices to the display processor 151 of the video stream providing device 15, such that the video stream providing device 15 displays the physiological indices by a form of graphs, diagrams, and/or numeric values (as FIG. 3 shows).

It should be further understood that, the core processor 112 shown in FIG. 8 can be further provided with an activity index calculating unit 1123 (as shown in FIG. 4), a face recognition unit 1124 (as shown in FIG. 5), a health state evaluating unit 1125 (as shown in FIG. 6) therein. Moreover, the storage module 11S shown in FIG. 8 can also be particularly designed to have a first data base 11S1 and a second data base 11S2 as the like that are shown in FIG. 5.

Figure 9:
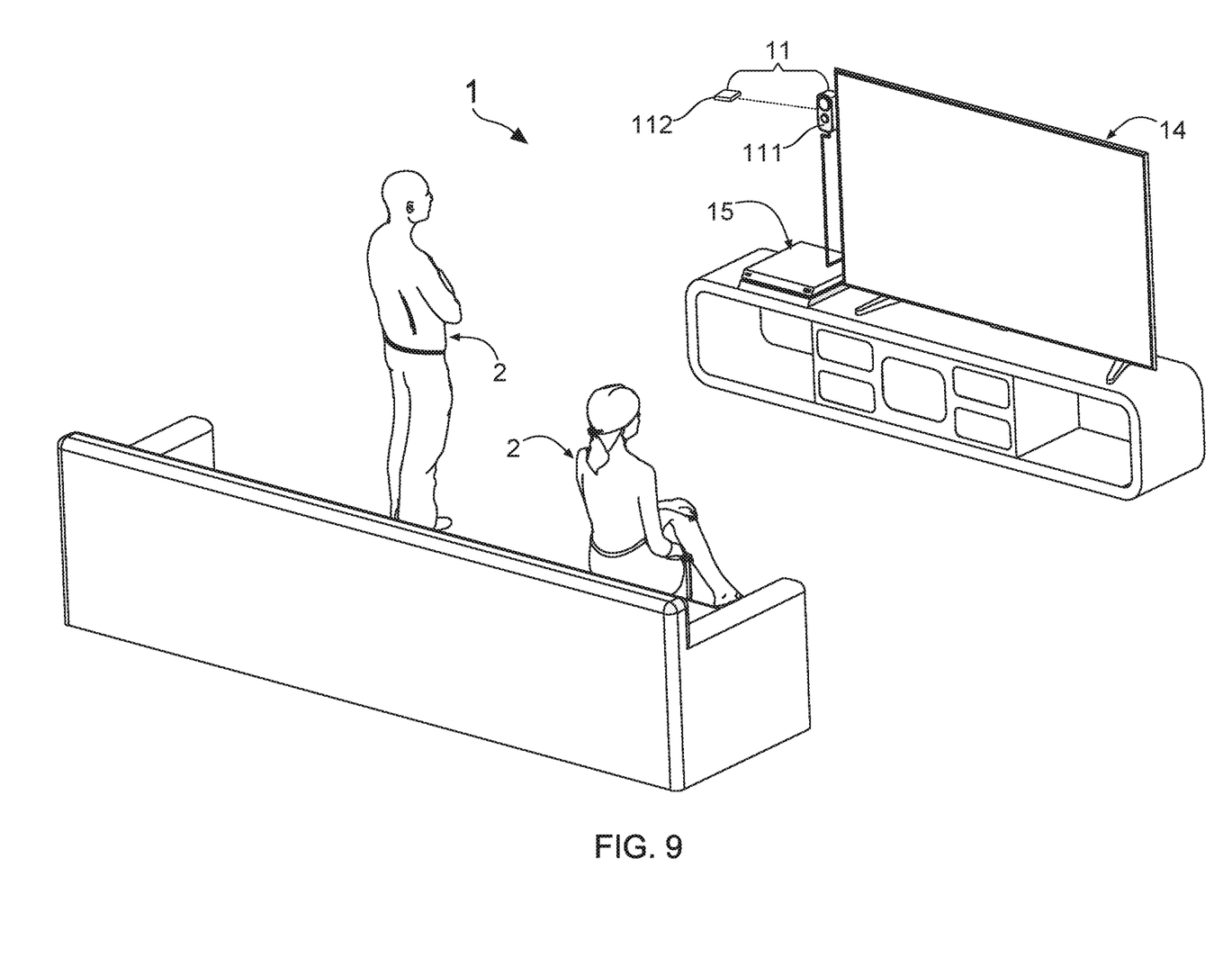
FIG. 9 shows a third stereo diagram of the home infotainment system having function of non-contact imaging-based physiological signal measurement according to the present invention.
Figure 10:
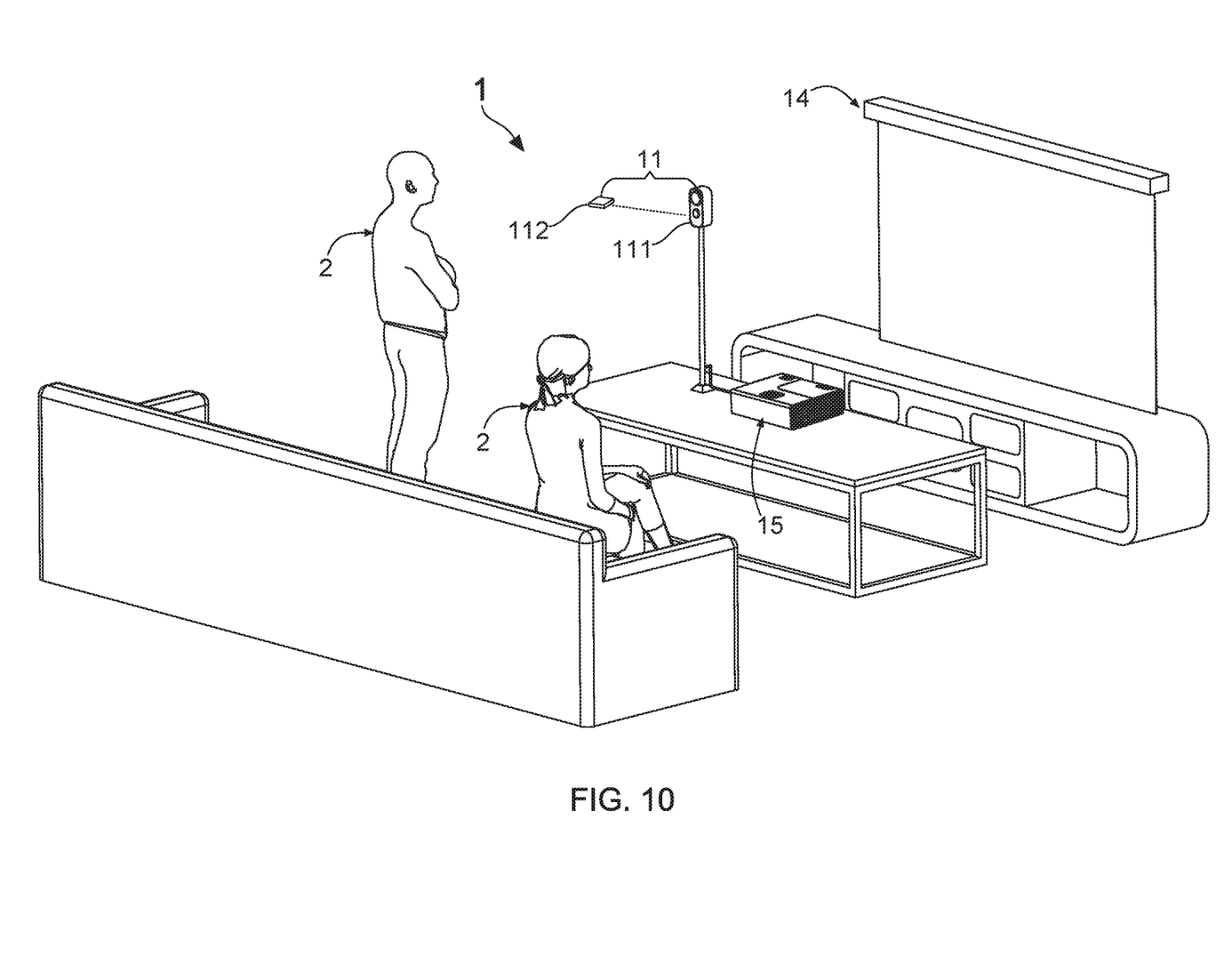
FIG. 10 shows a fifth block diagram of the home infotainment system having function of non-contact imaging-based physiological signal measurement according to the present invention.

Referring to FIG. 8 again, and please refer to FIG. 9 and FIG. 10, which respectively show a third stereo diagram and a fourth stereo diagram of the home infotainment system having function of non-contact imaging-based physiological signal measurement according to the present invention. From FIG. 8 and FIG. 9, it is known that the video stream providing device 15 can be a home video game console in one practicable embodiment, such that the display device 14 is facilitated to display a video of game that are transmitted from the home video game console. On the other hand, FIG. 8 and FIG. 10 indicate that the video stream providing device can also be a projection device on another one embodiment. In such case, the display device 14 is correspondingly a projection screen. As such, the video stream providing device 15 (projection device is coupled to a display source, so as to make the display device 14 (projection screen) to display a video based on the display source.

Therefore, through above descriptions, all embodiments and their constituting elements of the home infotainment system proposed by the present invention have been introduced completely and clearly. The above description is made on embodiments of the present invention. However, the embodiments are not intended to limit scope of the present invention, and all equivalent implementations or alterations within the spirit of the present invention still fall within the scope of the present invention.

What is claimed is:

1. A home infotainment system having function of non-contact imaging-based physiological signal measurement, comprising:
   a television; and
   an image-based physiological signal measuring device, being coupled to a display processor of the television, and comprising a camera that is configured for facing at least one user who is watching the television, so as to capture at least one image frame of the user; wherein the image-based physiological signal measuring device further comprises a core processor coupled to the camera, and the core processor comprising:
   a sensing portion detecting unit, being used for receiving the at least one image frame that is transmitted from the camera, thereby detecting a face portion from the image frame; and
   a physiological index calculating unit, being coupled to the sensing portion detecting unit, and being configured for extracting at least one physiological signal from the face portion, so as to subsequently calculate a plurality of physiological indices after applying at least one signal process to the physiological signal;
   wherein the plurality of physiological indices comprises heart rate, respiratory rate, heart rate variability (HRV), blood volume, arterial oxygen saturation, blood pressure, blood vessel viscosity, venous function, venous reflux, ankle pressure, genital response, and cardiac output, and the core processor being further configured for applying a data process to the plurality of physiological indices;
   wherein the data process is selected from a group consisting of data storing, data transmitting, displaying the physiological indices by a form of graphs or diagrams, and displaying the physiological indices by a form of numeric values.

2. The home infotainment system of claim 1, wherein the sensing portion detecting unit is also configured for detecting a chest portion from the image frame, such that physiological index calculating unit is able to extract the physiological signal from the chest portion, so as to subsequently calculate a respiratory rate of the user.

3. The home infotainment system of claim 1, wherein the core processor further comprises an activity index calculating unit, and the activity index calculating unit being coupled to the physiological index calculating unit, so as to calculate a plurality of activity indices of the user based on the plurality of physiological indices.

4. The home infotainment system of claim 3, wherein the core processor further comprises a face recognition unit, and the face recognition unit being coupled to the sensing portion detecting unit, so as to extract at least one facial feature of the user from the face portion that is found out by the sensing portion detecting unit, thereby completing a comparison between a plurality of reference facial features that are stored in the storage module and the facial feature.

5. The home infotainment system of claim 4, wherein the storage module comprises:
   a first data base for storing a plurality of user identity lists and the plurality of reference facial features, wherein each of the plurality of user identity lists has the corresponding reference facial features thereof; and
   a second data base for storing the plurality of activity indices and the plurality of physiological indices according to the plurality of user identity lists.

6. The home infotainment system of claim 5, wherein the core processor further comprises a health state evaluating unit, and the health state evaluating unit being coupled to the activity index calculating unit and the physiological index calculating unit, so as to complete a health state evaluation of the user based on the plurality of activity indices and the plurality of physiological indices.

7. A home infotainment system having function of non-contact imaging-based physiological signal measurement, comprising:
   a display device;
   a video stream providing device, being coupled to a display source, and being used for making the display device to display a video based on the display source; and
   an image-based physiological signal measuring device, being coupled to a display processor of the video stream providing device, and comprising a camera that is configured for facing at least one user who is watching the display device, so as to capture at least one image frame of the user; wherein the image-based physiological signal measuring device further comprises a core processor module coupled to the camera, and the core processor comprising:
   a sensing portion detecting unit, being used for receiving the at least one image frame that is transmitted from the camera, thereby detecting a face portion from the image frame; and
   a physiological index calculating unit, being coupled to the sensing portion detecting unit, and being configured for extracting at least one physiological signal from the face portion, so as to subsequently calculate a plurality of physiological indices after applying at least one signal process to the physiological signal;
   wherein the plurality of physiological indices comprises heart rate, respiratory rate, heart rate variability (HRV), blood volume, arterial oxygen saturation, blood pressure, blood vessel viscosity, venous function, venous reflux, ankle pressure, genital response, and cardiac output, and the core processor being further configured for applying a data process to the plurality of physiological indices;

wherein the data process is selected from a group consisting of data storing, data transmitting, displaying the physiological indices by a form of graphs or diagrams, and displaying the physiological indices by a form of numeric values.

8. The home infotainment system of claim 7, wherein the video stream providing device is selected from a group consisting of digital set-up box, home video game console and projection device, and the display device being selected from a group consisting of television, projection screen, LCD display device, LED display device, QD-LED display device, and OLED display device.

9. The home infotainment system of claim 7, wherein the sensing portion detecting unit is also configured for detecting a chest portion from the image frame, such that physiological index calculating unit is able to extract the physiological signal from the chest portion, so as to subsequently calculate a respiratory rate of the user.

10. The home infotainment system of claim 7, wherein the core processor further comprises an activity index calculating unit, and the activity index calculating unit being coupled to the physiological index calculating unit, so as to calculate a plurality of activity indices of the user based on the plurality of physiological indices.

11. The home infotainment system of claim 10, wherein the core processor further comprises a face recognition unit, and the face recognition unit being coupled to the sensing portion detecting unit, so as to extract at least one facial feature of the user from the face portion that is found out by the sensing portion detecting unit, thereby completing a comparison between a plurality of reference facial features that are stored in the storage module and the facial feature.

12. The home infotainment system of claim 10, wherein the storage module comprises:

a first data base for storing a plurality of user identity lists and the plurality of reference facial features, wherein each of the plurality of user identity lists has the corresponding reference facial features thereof; and a second data base for storing the plurality of activity indices and the plurality of physiological indices according to the plurality of user identity lists.

13. The home infotainment system of claim 12, wherein the core processor further comprises a health state evaluating unit, and the health state evaluating unit being coupled to the activity index calculating unit and the physiological index calculating unit, so as to complete a health state evaluation of the user based on the plurality of activity indices and the plurality of physiological indices.

\* \* \* \* \*